United States Patent [19]
Armstrong et al.

[11] Patent Number: 5,861,009
[45] Date of Patent: Jan. 19, 1999

[54] IMPLANTABLE CARDIAC STIMULATOR WITH RATE-ADAPTIVE T-WAVE DETECTION

[75] Inventors: Randolph K. Armstrong; Douglas J. Cook, both of Missouri City; Joseph W. Vandegriff, Brazoria, all of Tex.

[73] Assignee: Sulzer Intermedics, Inc., Angleton, Tex.

[21] Appl. No.: 955,411

[22] Filed: Oct. 21, 1997

[51] Int. Cl.⁶ ..................................................... A61N 1/365
[52] U.S. Cl. ............................................................. 607/17
[58] Field of Search ................................ 607/17, 18–26, 607/4; 600/509

[56] References Cited

U.S. PATENT DOCUMENTS

| | | | |
|---|---|---|---|
| 4,830,006 | 5/1989 | Haluska et al. | 128/419 |
| 5,413,592 | 5/1995 | Schroeppel | 607/18 |

OTHER PUBLICATIONS

Physician's System Manual; *Ventak AV 1810/1815*; Guidant Corporation; 1986.

*Primary Examiner*—William E. Kamm
*Assistant Examiner*—Kennedy J. Schaetzle
*Attorney, Agent, or Firm*—John R. Merkling; Conley, Rose & Tayon

[57] ABSTRACT

An implantable device for providing pacing and defibrillating stimuli to a heart, comprises: a power source, at least one electrode electrically connected to said power source, a sensor capable of providing data that can be used to determine a physiological pacing demand, and a control device. The control device controls the application of electrical stimuli to the heart. The control device calculates an adjusted pacing interval based on said demand, calculates an adjusted ventricular pace refractory period ($VPRP_{current}$) that is a function of said pacing interval, and calculates a T-wave monitoring window. The end time, and optionally the start time also, of the T-wave window is a function of the pacing interval. The control device is also capable of adjusting the sensitivity of an amplifier based on signals received during the T-wave window.

23 Claims, 4 Drawing Sheets

IMPLANTABLE CARDIAC STIMULATOR WITH RATE-ADAPTIVE T-WAVE DETECTION

BACKGROUND OF THE INVENTION

A. Field of the Invention

The present invention relates generally a cardiac stimulating device that combines the abilities and objectives of implantable pacemakers and defibrillators. More particularly, the present invention relates to a implantable cardioverter/defibrillator that is capable of both rate responsive pacing and detection of fibrillation. Still more particularly, the present invention relates to a cardiac stimulating device that includes a rate-responsive adjustment of the T-wave window, which is in turn used to automatically adjust the sensitivity, or gain of the device.

B. Description of the Related Art

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacing and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device that delivers electrical pulses to an electrode that stimulates the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. Implanted pacemakers can either pace continuously, or can be provided with sensors that are able to detect a natural pacing signal, allowing the implanted device to be inhibited from pacing when artificial pacing stimulus is not needed. Pacing in this manner is known as demand pacing, in that the pacer only provides a pacing stimulus when it fails to detect a natural pacing signal.

In addition, pacers today are often rate responsive on the basis of sensor input. That is, one or more physiological parameters are measured and used as a basis for calculating an optimal pacing rate. Thus, the rate at which this type of rate responsive demand pacer looks for natural pacing signals depends on the value of the physiological parameter (s) being tracked. This produces an effect similar to that in dual chamber pacemakers in which the ventricular pacing rate increases as it "tracks" increases in the atrial rate. An in-depth explanation of certain cardiac physiology and pacemaker theory of operation is provided in U.S. Pat. No. 4,830,006. Throughout the following discussion and claims, the concepts of "rate responsiveness" and "pacing demand" refer to and include both sensor-driven and "tracked" types of systems.

Cardiac ventricular fibrillation is a condition characterized by rapid, chaotic electrical and mechanical activity of the heart's excitable myocardial tissue that results in uncoordinated activity of the heart tissue and consequent ineffectual quivering of the ventricles. This in turn causes an instantaneous cessation of blood flow from the heart. Unless cardiac output is restored almost immediately after the onset of ventricular fibrillation, tissue begins to die for lack of oxygenated blood and patient death can occur within minutes.

Defibrillation is a technique involving the application of one or more high energy electrical stimuli to the heart in an effort to overwhelm the chaotic contractions of individual tissue sections and to restore the synchronized contraction of the total mass of heart tissue. Successful defibrillation requires the delivery of a sufficient electrical pulse to the heart of the patient to terminate fibrillation and preclude immediate re-emergence of the condition.

The use of implantable defibrillators for treating cardiac fibrillation is well known. Likewise, devices capable of delivering both demand pacing pulses and defibrillation shocks are known and are indicated for heart patients suffering from both irregular heart beat and occasional cardiac fibrillation.

Conventional pacemakers and implantable cardioverter/defibrillators (ICD's) typically operate by analyzing the electrical output of the heart in a series of windows. Referring now to FIG. 2, a portion of an external electrocardiograph showing two complete pacing cycles is labeled so as to illustrate the component parts of each cycle. A cycle begins with a P-wave, which indicates an atrial event, followed by a QRS wave indicative of ventricular contraction. The cycle ends with a T-wave caused by repolarization of the ventricles in preparation for the next cycle. A ventricular demand pacemaker looks for the R-wave that indicates a natural pacing or "sensed" event. When a sensed event occurs, the pacer is inhibited from providing an unnecessary pacing stimulus.

It is common for pacers and ICD's to use a ventricular pace refractory period (VPRP), during which ventricular activity is ignored. The VPRP helps prevent misinterpretation of post-pace electrical activity or T-waves as R-waves and creates a monitoring window for T-wave activity. Early pacers commonly used a fixed VPRP. Many dual-chamber and rate-responsive pacers still use a fixed VPRP, however, the VPRP in these devices is limited by the maximum possible ventricular pacing rate. That is, the VPRP must be shorter than the shortest possible pacing interval. Thus, the fixed VPRP may not be completely appropriate for all of the pacing rates that the pacer can deliver. To address this problem, it is known to dynamically adjust the VPRP in proportion to the pacing interval, allowing a longer VPRP to be used at slower pacing rates.

On the other hand, because the amplitude of the signals generated by the ventricles during fibrillation are so much smaller than the amplitude of signals generated during normal operation (either paced or sensed), there is a possibility that device may not be able to detect fibrillation signals during rapid ventricular pacing. If the device cannot detect fibrillation signals and thereby distinguish fibrillation from bradycardia, there is a possibility that the needed defibrillation therapy will not be administered. One solution to this problem is to adjust the gain of the sensing amplifier in response to changes in the amplitude of T-wave. Thus, it is desirable to use T-wave amplitude and/or timing data collected during the T-wave monitoring window within the VPRP to calculate, among other things, the degree to which gain should be adjusted. Because the physiologic delay from pace to T-wave is often proportional to the pacing interval, at slower ventricular pacing rates, the T-wave may occur too late in the fixed VPRP to be completely detected if the fixed VPRP is too short.

Thus, many of the approaches taken to address the problems related to rate-responsive pacing also have the undesired effect of reducing the reliability of the T-wave data. Hence, it is desired to provide a technique for ensuring that collection of T-wave data is optimized for all possible pacing/defibrillating modes and at all foreseeable pacing rates.

SUMMARY OF THE INVENTION

The present invention comprises an implantable device capable of both rate-responsive pacing and defibrillation as needed. The device includes a dynamically adjustable VPRP that corresponds to the adjusted pacing rate, which in turn corresponds to the measured physical activity level of the patient (demand). The present invention further includes a dynamically adjustable T-wave monitoring window that is designed to optimally collect the T-wave data within the adjusted VPRP. The T-wave window is adjusted in response to changes in the pacing rate. The present device further includes a T-wave sensor that provides a measurement of the T-wave amplitude, which in turn can be used to adjust the gain or sensitivity of the device. The rate-responsive adjusted pacing rate is calculated in a known manner, based on one or more measured physiological indicators.

BRIEF DESCRIPTION OF THE DRAWINGS

Other objects and advantages of the invention will become apparent upon reading the following detailed description and upon reference to the accompany drawings, wherein.

DETAILED DESCRIPTION OF THE INVENTION

According to the present invention an implantable rate-responsive pacer/cardioverter/defibrillator is provided with an adjustable ventricular pace refractory period (VPRP) that varies as a function of the adjusted pacing rate and an adjustable gain control that adjusts the sensitivity of the device in response to changes in the amplitude of the T-wave signal. As stated above, a preferred embodiment includes a rate-responsive feature that calculates an adjusted pacing rate that is greater than the programmed base pacing rate, based on measured physiological demand data, such as activity or blood oxygen level.

Figure 1:
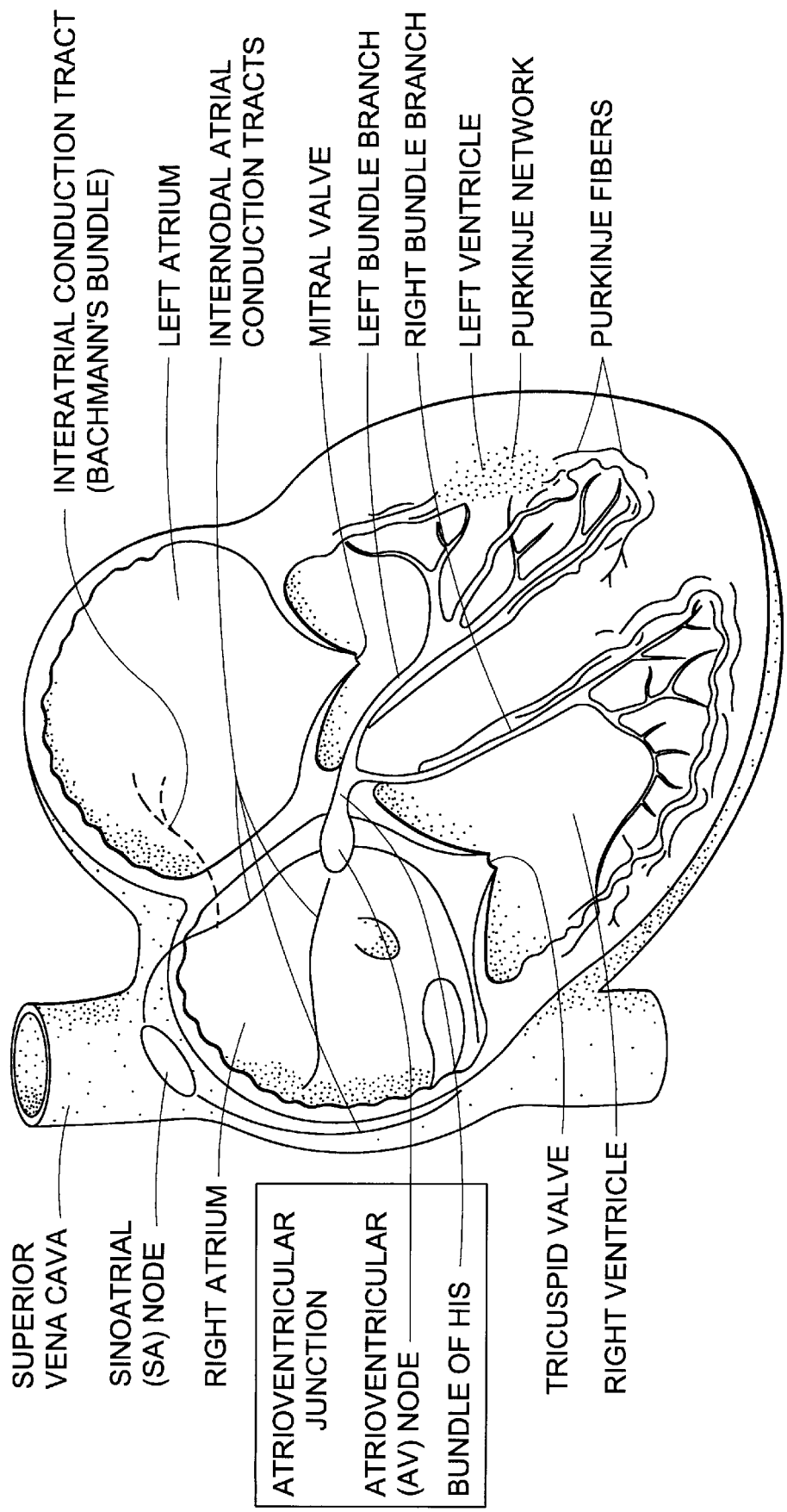
FIG. 1 is a schematic cut-away view of a human heart, in which the various relevant parts are labeled.
Figure 2:
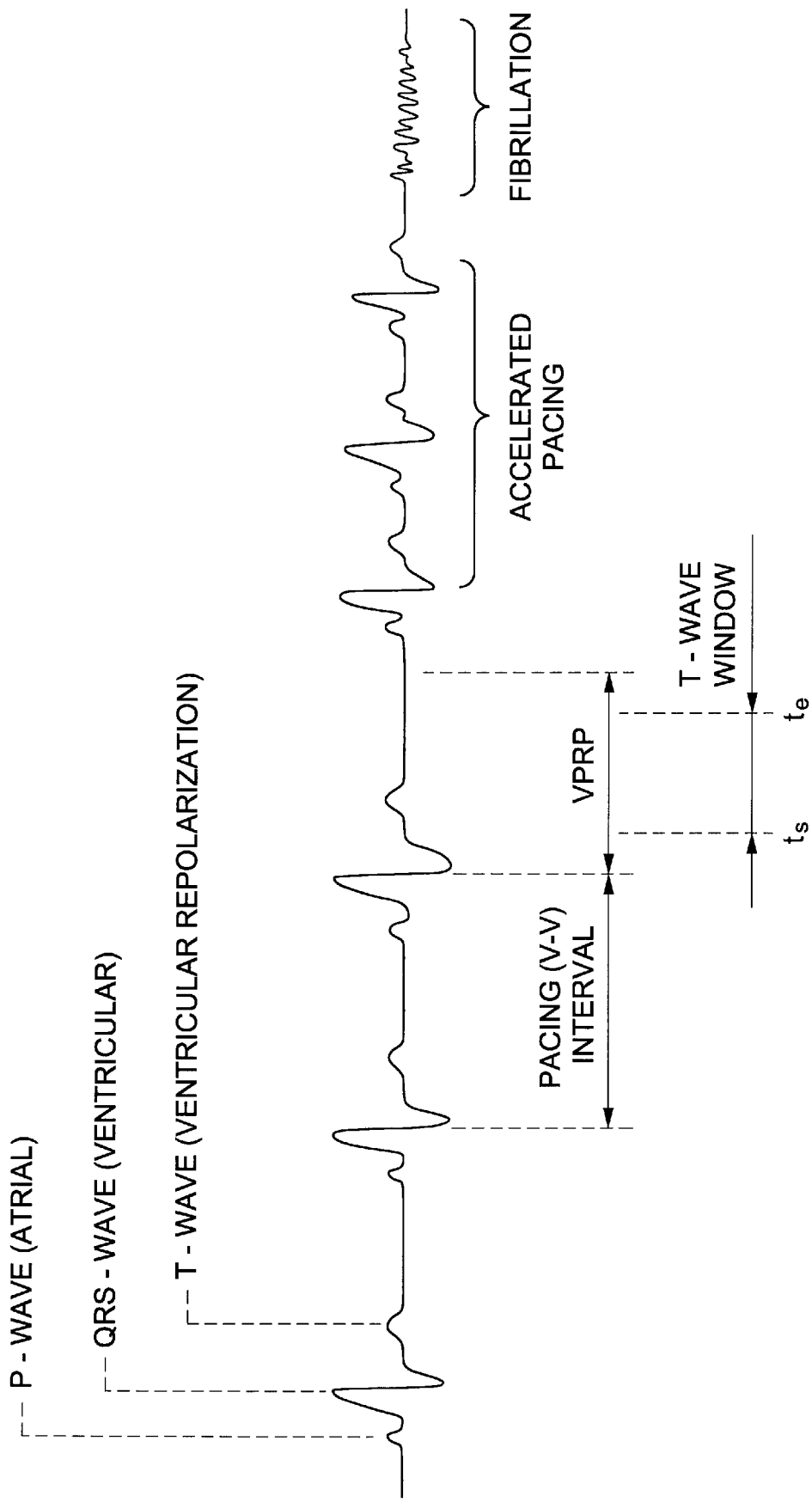
FIG. 2 shows an exemplary external electrogram during normal sinus rhythm and during fibrillation.
Figure 3:
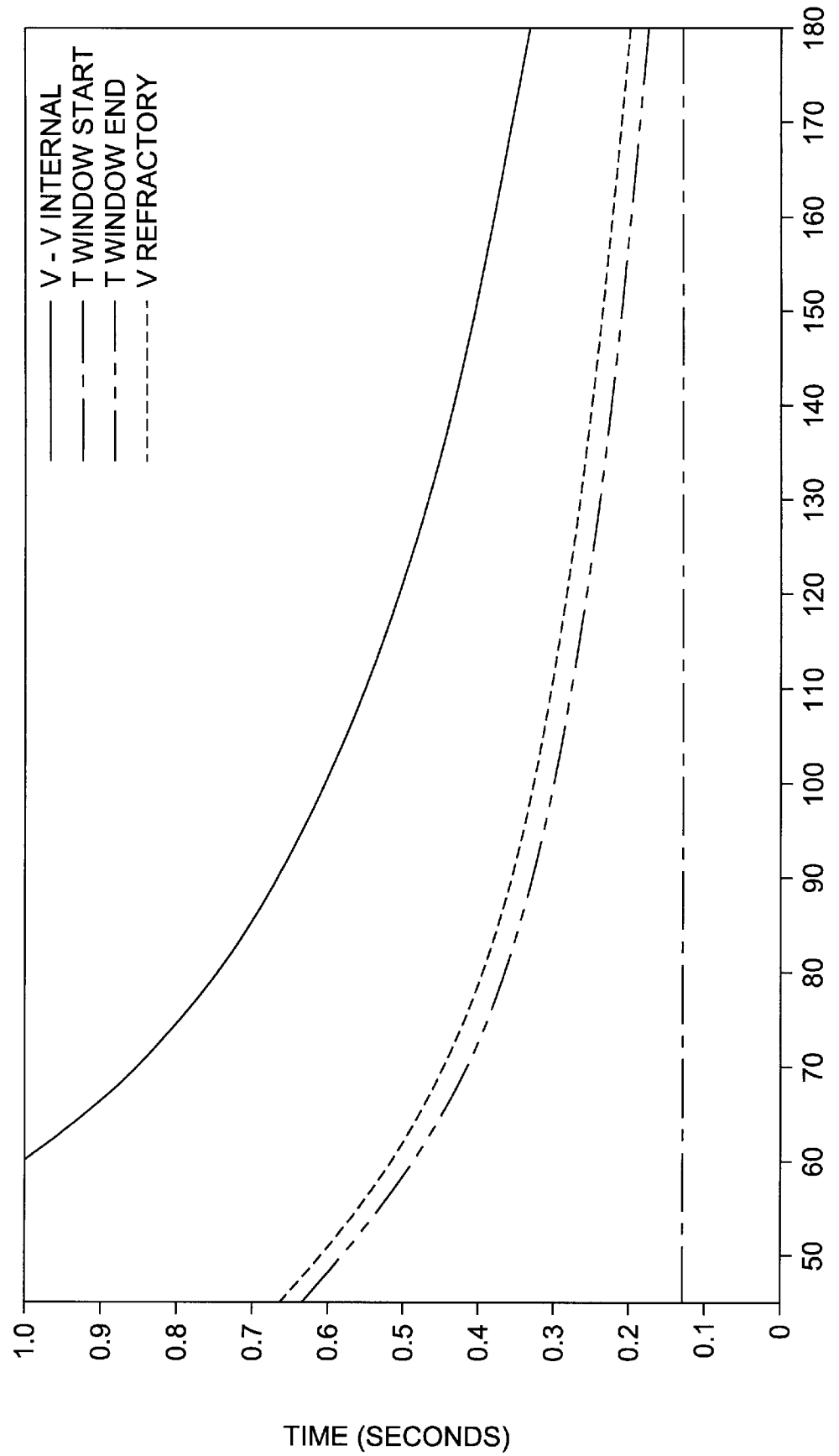
FIG. 3 is a plot showing the variation of the VPRP and T-wave window in accordance with one embodiment of the present invention.

Referring now to FIGS. 2 and 3, according the present invention, an implantable device is provided with an adjustable VPRP that is a function of the adjusted pacing rate. Thus:

$$VPRP = f_1(\text{adjusted pacing rate})$$

While it will be understood that the principles described herein are generally applicable to a variety of devices, they are primarily advantageous in rate-responsive devices, i.e. those that vary the pacing rate in response to demand by the body. The V—V interval is measured from the beginning of each R-wave for either a sensed or a paced event and all other periods or intervals discussed hereinafter are calculated and expressed in terms of the same time interval, namely the interval beginning with a ventricular pace or sense event and ending at the next ventricular pace or sense event. When the pacemaker is pacing the heart, this interval will have a duration of $(\text{pacing rate})^{-1}$. It will be understood that, when the pacing rate is given in ppm, the interval as referred to herein is calculated as $60{,}000 \times (\text{pacing rate})^{-1}$, which gives an interval having units of msec.

Within the span of the VPRP, the present invention includes an adjustable T-wave monitoring window that begins at $t_s$ and ends at $t_e$, with $t_s$ and $t_e$ being defined as functions of the adjusted pacing rate:

$$t_s = f_2(\text{adjusted pacing rate})$$

$$t_e = f_3(\text{adjusted pacing rate})$$

and the duration of the T-wave monitoring window being equal to $t_e - t_s$.

According to one preferred embodiment, the adjusted VPRP for a given pacing rate, $VPRP_{current}$, is calculated as follows:

$$VPRP_{current} = VPRP_{base} - (I_{base} - I_{current}) \left[ \frac{VPRP_{base} - VPRP_{max}}{I_{base} - I_{max}} \right]$$

where:

$I_{base}$ is the interval of the baseline (lowest) bradycardia pacing rate, $I_{max}$ is the interval of the maximum pacing rate, $I_{current}$ is the interval of the current (adjusted) pacing rate, $VPRP_{base}$ is the programmed VPRP for the baseline (lowest) bradycardia pacing rate, and $VPRP_{max}$ is the programmed VPRP for the maximum pacing rate.

In a pacer that has been programmed for a particular patient, $I_{base}$, $I_{max}$, $VPRP_{base}$, and $VPRP_{max}$ will be programmed constants, while $I_{current}$ will vary with demand. Thus, in this embodiment, $VPRP_{current}$ is linearly proportional to the difference between the baseline pacing interval and the current pacing interval.

According to this embodiment, the physician initially programs the device with set values for the baseline (lowest) bradycardia pacing rate $(I_{base})^{-1}$, the maximum pacing rate $(I_{max})^{-1}$, the $VPRP_{base}$ corresponding to the baseline pacing rate, and the $VPRP_{max}$ corresponding to the maximum pacing rate. From these four fixed values, plus the input from the activity/demand sensor(s), all of the remaining variables, $I_{current}$, $VPRP_{current}$, $t_e$ and $t_s$ can be calculated on a continuous basis by the device.

According to one preferred embodiment, $t_s$ is programmed to be a constant, rather than a function of the pacing rate, such as for example 130 msec, and $t_e$ is programmed to be equal to $VPRP_{current}$ minus a constant, such as for example:

$$t_e = VPRP_{current} - 25.6 \text{ msec.}$$

FIG. 3 shows the operation of a device in accordance with this embodiment. Line 10 indicates the V—V interval, or base pacing rate, on which the other intervals described herein are based. As stated above, the V—V interval is dependent on the physiological demands of the patient and is calculated in accordance with known rate calculation techniques. Line 12 indicates the duration of the VPRP, line 14 indicates the end of the T-wave monitoring window $t_e$ and line 16 indicates the start of the T-wave monitoring window $T_s$. Line 16 is a constant in the illustrated embodiment, having the value assigned above. The values of each of the variables $I_{current}$, $VPRP_{current}$ and $t_e$ can be found for a given pacing rate by taking the value of each line 10, 12 and 14 at the point where it intersects a vertical line drawn through that pacing rate.

In FIG. 3, which is illustrative only and not intended to limit the scope of the invention, the programmed values discussed above were assigned the following values: baseline bradycardia pacing rate=45 ppm, maximum pacing rate=180 ppm, $r_{base}$=665 msec and $r_{max}$=200 msec. This fixes the constant multiplier in Equation (1) at approximately one-half for this example.

While the foregoing embodiment defines the $VPRP_{current}$ as proportional to the difference between the maximum and adjusted pacing intervals, it will be understood that the function relating $VPRP_{current}$ to the V—V interval need not be linear, and can be any other type of function that yields a $VPRP_{current}$ that is less than the corresponding V—V interval. Similarly, while the end of the T-wave monitoring window $t_e$ is described above as $VPRP_{current}$ minus a constant, it could alternatively be defined as any other linear or non-linear function of $VPRP_{current}$ or the adjusted pacing rate that yields a $t_e$ that is less than $VPRP_{current}$. Similarly, while the start of the T-wave monitoring window $T_s$ is described above as a constant time value, it could alternatively be defined as any linear or non-linear function of $VPRP_{current}$ or the adjusted pacing rate, so long as $t_s$ remains less than $t_e$. Examples of instances in which it may be desired to use a non-constant $t_s$ include occurrences of problematic post-pace lead polarization.

Figure 4:
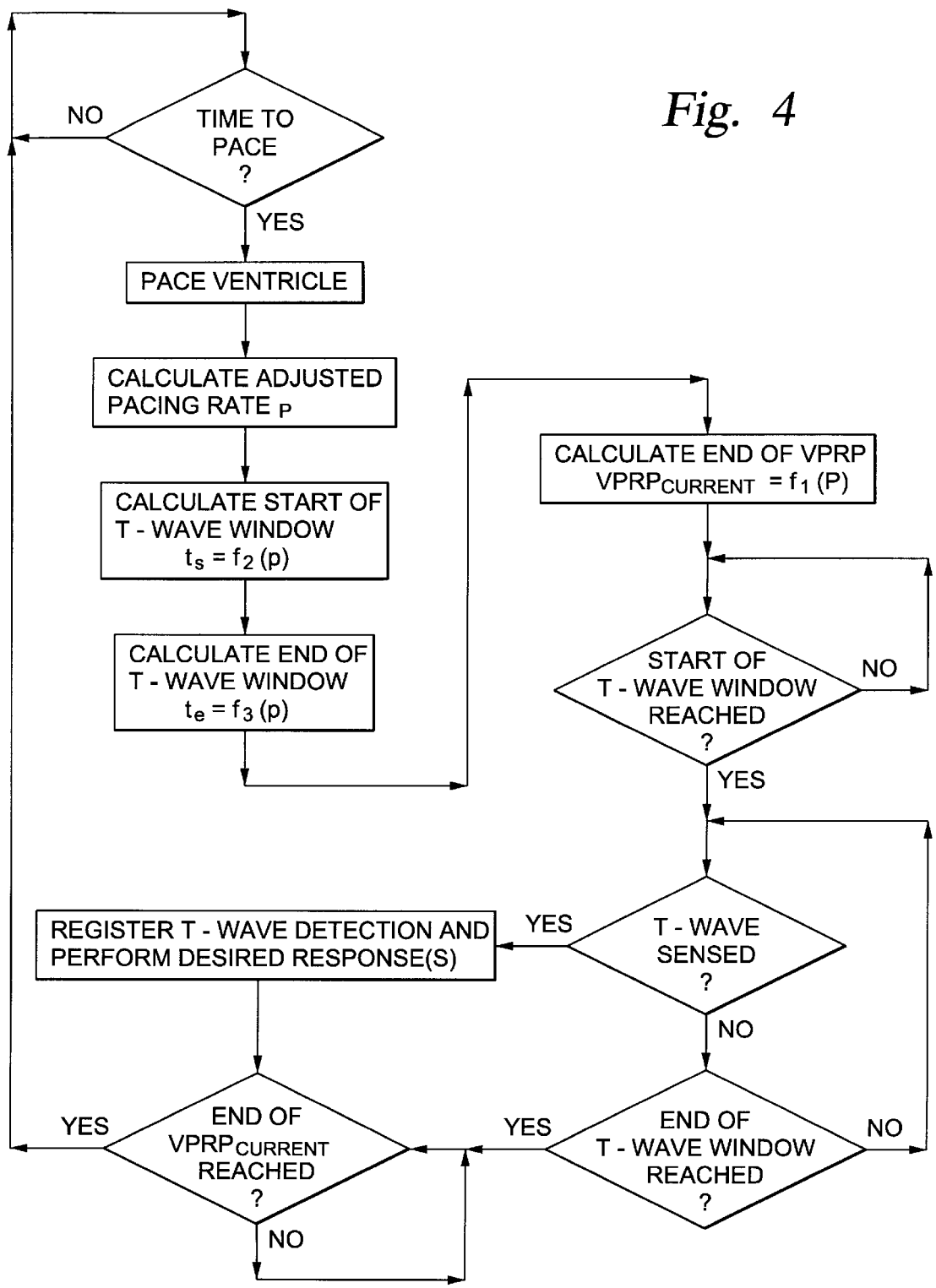
FIG. 4 is a flow chart representing the steps for ventricular pacing in accordance with the present invention.

Referring now to FIG. 4, a flow chart reflecting the concepts described above illustrates how the calculated start and end times for the dynamically adjustable T-wave window are used. This adjustable T-wave window helps ensure that the T-wave window is timed so as to maximize the probability that the T-wave will be deeted, regardless of the current pacing rate.

While a preferred embodiment of the present invention is set out above, it will be understood that variations may be made to the present method without departing from the scope of the invention. Thus, while one mode of operation of the invention has been explained in what is now considered to represent its best embodiments, which have been illustrated and described, it should be understood that within the scope of the appended claims the invention may be practiced otherwise than as specifically illustrated and described.

What is claimed is:

1. An implantable device for providing pacing and defibrillating stimuli to a heart, comprising:

a power source;

at least one electrode electrically connected to said power source;

a sensor capable of providing data that can be used to determine a physiological pacing demand; and a control device, said control device controlling the application of electrical stimuli through said electrode, said control device calculating a physiological pacing demand based on said data, calculating an adjusted pacing interval based on said demand, calculating an adjusted ventricular pace refractory period ($VPRP_{current}$) that is a function of said pacing interval, and calculating the end time of a T-wave monitoring window, said end time being a function of said pacing interval and being less than said $VPRP_{current}$.

2. The implantable device according to claim 1 wherein said control device also calculates the start time of a T-wave monitoring window.

3. The implantable device according to claim 2 wherein said start time is a function of said pacing interval and is less than said end time.

4. The implantable device according to claim 2 wherein said start time is a constant.

5. The implantable device according to claim 1 wherein said $VPRP_{current}$ is proportional to the difference between a baseline pacing interval and the adjusted pacing interval.

6. The implantable device according to claim 1, further including a detector that detects T-waves that occur before said end time.

7. The implantable device according to claim 6, further including an amplifier with an adjustable gain, wherein said gain is adjusted in response to changes in the amplitude of signals detected by said detector.

8. The implantable device according to claim 1 wherein said end time is a function of said $VPRP_{current}$.

9. A method for monitoring a heart, comprising:

(a) sensing data that can be used to determine a pacing demand;

(b) calculating an adjusted pacing interval based on the demand;

(c) calculating an adjusted ventricular pace refractory period ($VPRP_{current}$) that is a function of the pacing interval;

(d) calculating the end time of a T-wave monitoring window, the end time being a function of the pacing interval and being less than the $VPRP_{current}$;

(e) providing the start time of the T-wave window; and (f) monitoring electrical signals emitted by the heart during the period between the start time and the end time of the T-wave window.

10. The method according to claim 9 wherein the monitoring of step (f) is carried out so as to detect T-waves.

11. The method according to claim 9, further including the step of adjusting the gain of a signal amplifier in response to changes in the amplitude of signals detected during step (f).

12. The method according to claim 9, further including the step of controlling the application of electrical stimuli through the electrode so as to correspond to the adjusted pacing interval.

13. The method according to claim 9 wherein step (e) is carried out by calculating a start time that is a function of the adjusted pacing interval.

14. The method according to claim 9 wherein step (e) is carried out by calculating a start time that is a function of the end time.

15. A control device for an implantable cardioverter/defibrillator that is also capable of providing pacing stimuli to a heart at a demand-responsive adjusted pacing interval, said control device controlling the application of electrical stimuli to the heart, said control device calculating the adjusted pacing interval of the rate-responsive pacing, calculating an adjusted ventricular pace refractory period ($VPRP_{current}$) that is a function of said adjusted pacing interval, and calculating the end time of a T-wave monitoring window, said end time being a function of said adjusted pacing interval and being less than said $VPRP_{current}$.

16. The control device according to claim 15 wherein said control device also calculates the start time of a T-wave monitoring window.

17. The control device according to claim 16 wherein said start time is a function of said pacing interval and is less than said end time.

18. The control device according to claim 16 wherein said start time is a constant.

19. The control device according to claim 15 wherein said $VPRP_{current}$ is proportional to the difference between a baseline pacing interval and the adjusted pacing interval.

20. The control device according to claim 15, further including a detector that detects signals that occur before said end time of said T-wave window.

21. The control device according to claim 20, further including an amplifier with an adjustable gain, wherein said gain is adjusted in response to changes in the amplitude of signals detected by said detector.

22. The device according to claim 15 wherein said end time is a function of said $VPRP_{current}$.

23. An implantable device for providing pacing and defibrillating stimuli to a heart, comprising:

a power source;

at least one electrode electrically connected to said power source;

a sensor capable of providing data that can be used to determine a physiological pacing demand; and a control device, said control device controlling the application of electrical stimuli through said electrode, said control device calculating a physiological pacing demand based on said data, calculating an adjusted pacing interval based on said demand, calculating an adjusted ventricular pace refractory period ($VPRP_{current}$) that is a function of said pacing interval, and calculating the end time of a T-wave monitoring window, said end time being a function of said pacing interval and being less than said $VPRP_{current}$.

* * * * *